United States Patent
Ahn

(10) Patent No.: US 12,226,265 B2
(45) Date of Patent: Feb. 18, 2025

(54) METHOD FOR MANUFACTURING MARKER WITH AERATED HYDROGEL

(71) Applicant: Devicor Medical Products, Inc., Cincinnati, OH (US)

(72) Inventor: Harry Kyuhoon Ahn, Liberty Township, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 890 days.

(21) Appl. No.: 17/373,906

(22) Filed: Jul. 13, 2021

(65) Prior Publication Data

US 2021/0338369 A1 Nov. 4, 2021

Related U.S. Application Data

(62) Division of application No. 16/131,346, filed on Sep. 14, 2018, now Pat. No. 11,090,132.

(60) Provisional application No. 62/559,088, filed on Sep. 15, 2017.

(51) Int. Cl.
| | |
|---|---|
| A61L 31/14 | (2006.01) |
| A61B 90/00 | (2016.01) |
| A61K 49/04 | (2006.01) |
| A61K 49/18 | (2006.01) |
| A61L 31/18 | (2006.01) |
| C08J 9/30 | (2006.01) |

(52) U.S. Cl.
CPC .............. *A61B 90/39* (2016.02); *A61K 49/04* (2013.01); *A61K 49/1803* (2013.01); *A61L 31/145* (2013.01); *A61L 31/146* (2013.01); *A61L 31/148* (2013.01); *A61L 31/18* (2013.01); *C08J 9/30* (2013.01); *A61B 2090/3908* (2016.02); *A61B 2090/3933* (2016.02); *C08J 2205/022* (2013.01); *C08J 2207/10* (2013.01); *C08J 2300/16* (2013.01)

(58) Field of Classification Search
CPC .............................. B01F 11/071; A61B 90/39
See application file for complete search history.

(56) References Cited

U.S. PATENT DOCUMENTS

| | | | |
|---|---|---|---|
| 10,610,841 B1 * | 4/2020 | Zimmer | A61K 49/226 |
| 12,042,772 B2 * | 7/2024 | Zimmer | B01F 31/65 |
| 2010/0193547 A1 * | 8/2010 | Laidler | B29C 49/06 |
| | | | 222/207 |

* cited by examiner

*Primary Examiner* — Micah Paul Young
(74) *Attorney, Agent, or Firm* — Frost Brown Todd LLP

(57) ABSTRACT

A system for aerating a marker material. The system includes a first container, a second container, and an aeration connector. The aeration connector includes a body and a screen disk disposed within the body. The first container is in communication with the second container via the aeration connector. The screen disk of the aeration connector is configured to aerate a marker material as the marker material is repeatedly passed between the first container and the second container.

6 Claims, 8 Drawing Sheets

METHOD FOR MANUFACTURING MARKER WITH AERATED HYDROGEL

PRIORITY

This application is a divisional of U.S. Ser. No. 16/131,346 entitled "Method for Manufacturing Marker with Aerated Hydrogel," filed on Sep. 14, 2018, now published as U.S. Pub. No. 2019/0008606 on Jan. 10, 2019, which claims priority to U.S. Provisional Patent App. 62/559,088 entitled "Method for Manufacturing Marker with Aerated Hydrogel," filed Sep. 15, 2017, the disclosure of which is incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (typically a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The state of the art technology for conducting a breast biopsy is to use a vacuum-assisted breast biopsy device. A current textbook in this area is "Vacuum-Assisted Breast Biopsy with Mammotome®", available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

A biopsy marker may comprise hydrogel, such as described in "Evaluation of a Hydrogel Based Breast Biopsy Marker HydroMARK® as an Alternative to Wire and Radioactive Seed Localization for Non-Palpable Breast Lesions" by Rebecca L. Klein et al.; Journal of Surgical Oncology 2012; 105: 591-594, the contents of which are incorporated herein by reference.

Additional details regarding hydrogel are described in "Hydrogel: Preparation, characterization, and applications: A review" by Enas M. Ahmed; Journal of Advanced Research (2015) 6; 105-121, the contents of which are incorporated herein by reference.

The use of hydrogel materials for markers used after breast biopsies to mark the location where the biopsied tissue was removed is described and claimed in the following U.S. Pat. No. 6,083,524, "Polymerizable biodegradable polymers including carbonate or dioxanone linkages" issued Jul. 4, 2000; U.S. Pat. No. 6,162,241, "Hemostatic tissue sealants", issued Dec. 4, 2000; U.S. RE39713, "Polymerizable biodegradable polymers including carbonate or dioxanone linkages issued Jul. 3, 2007; U.S. Pat. No. 6,270,464, "Biopsy localization method and device", issued Aug. 7, 2001; U.S. Pat. No. 6,356,782, "Subcutaneous cavity marking device and method", issued Mar. 12, 2002; U.S. Pat. No. 6,605,294, "Methods of using in situ hydration of hydrogel articles for sealing or augmentation of tissue or vessels", issued Aug. 12, 2003; U.S. Pat. No. 6,790,185, "Sealant plug delivery methods", issued Sep. 14, 2004; U.S. Pat. No. 8,320,993 "Subcutaneous cavity marking device", issued Nov. 27, 2012; U.S. Pat. No. 8,600,481, "Subcutaneous cavity marking device", issued Dec. 3, 2013 and U.S. Pat. No. 8,939,910, "Method for enhancing ultrasound visibility of hyperechoic materials", issued Jan. 27, 2015. All of these US Patents are incorporated by reference in their entirety.

U.S. Pat. No. 8,939,910, "Method of Enhancing Ultrasound Visibility of Hyperechoic Materials", issued on 27 Jan. 2015 and assigned to Devicor Medical Products, Inc., the contents of which having previously been incorporated herein by reference, describes a hydrogel marker that is enhanced by air cavities within the hydrogel that reflect under ultrasound imaging in different way than the reflection of the hydrogel, thereby making it easier to detect the hydrogel marker. Such air cavities in the enhanced hydrogel are hypoechoic and thus serve to further indicate the location of the marker. U.S. Pat. No. 8,939,910 gives an example of creating air cavities using inserts of differing sizes and shapes. The inserts are placed in the hydrogel during the manufacturing process and removed from the hydrogel after it is cured, leaving air-filled cavities in the hydrogel marker. The cavities are air-filled and reflecting differently under ultrasound imaging from the reflection of the hydrogel and making the hydrogel easier to detect under ultrasound.

In some contexts, a marker element is disposed within a bioabsorbable carrier. In these contexts, it may be desirable to enhance the visibility of the carrier under ultrasonic visualization. One method of enhancing visualization of the carrier is impregnating the carrier with a plurality of microbubbles. However, some difficulties have been encountered with uniformly distributing microbubbles of a sufficient size throughout the carrier. Accordingly, in some contexts, it may be desirable to enhance a biopsy site marker by uniformly distributing microbubbles of a sufficient size throughout a carrier. While several systems and methods have been made and used for marking a biopsy site, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1A:
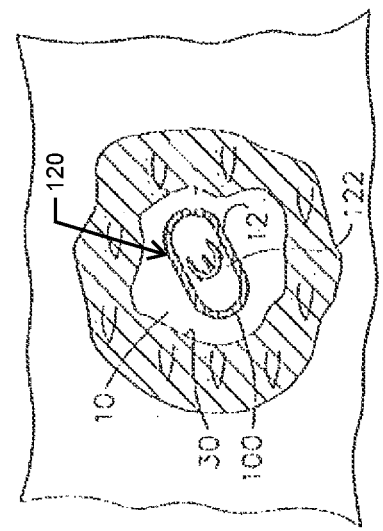
FIG. 1A depicts a cross-sectional view of an exemplary biopsy site marker for use in marking a biopsy site in a patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

Figure 1B:
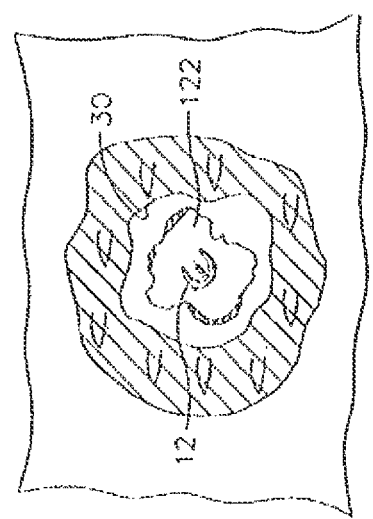
FIG. 1B depicts another cross-sectional view of the marker of FIG. 1A, with a marker material in a partially expanded configuration.
Figure 1C:
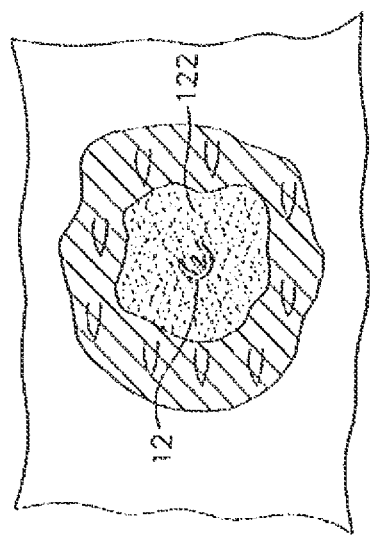
FIG. 1C depicts still another cross-sectional view of the marker of FIG. 1A, with the marker material in a fully expanded configuration.

Aspects presented herein relate to devices and procedures for manufacturing a marker for percutaneously marking a biopsy cavity (10) having surrounding tissue (30), as illustrated in FIGS. 1A-C. For instance, as seen in FIG. 1A, a marker (100) may be initially placed in the biopsy cavity (10) to facilitate relocation of the biopsy site. Marker (100) may comprise a carrier (120), which includes a marker material (122) that has been enhanced to comprise a plurality of bubbles or microbubbles. As will be described in greater detail below, such bubbles may be generally desirable to provide enhanced reflection of ultrasonic radiation from the interior and exterior of marker (100). As will be described in greater detail below, carrier (120) is generally bioabsorbable such that marker material (122) may be generally absorbed into the patient's tissue over time.

In the present example, marker (100) further includes a marker element (12) that is not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12).

As described above, carrier (120) of marker (100) may comprise a bioabsorbable marker material (122). In the present example, marker material (122) comprises a hydrogel that is initially in a dehydrated state. Although a hydrogel is used in the present example, it should be understood that in other examples marker material (122) may comprise other known bioabsorbable materials.

In the present example, marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) is typically delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) is preferably large enough to be readily visible to the physician under x-ray or ultrasonic viewing, for example, yet be small enough to be able to be percutaneously deployed into the biopsy cavity and to not cause any difficulties with the patient.

Although examples are described in connection with treatment and diagnosis of breast tissue, aspects presented herein may be used for markers in any internal, preferably soft, tissue, e.g., in breast tissue, lung tissue, prostate tissue, lymph gland tissue, etc.

Many properties of a marker material affect the intensity of its ultrasound reflection, including density, physical structure, molecular material, and shape. For example, sharp edges, or multiple reflecting surfaces on or within an object differing in density from its surroundings enhances a marker's ability to be detected by ultrasound. Interfaces separating materials of different densities, such as between a solid and a gas, produce strong ultrasound signals.

A typical human breast has a substantial number of features that are visualized with ultrasound. These features all have characteristic signals. Fibrous tissue or ligaments tend to show up as bright streaks, fat seems to appear as a dark gray area, the glandular tissue appears as a mottled medium gray mass. Cancerous lesions typically appear as a darker area with a rough outer edge that has reduced through transmission of the ultrasound energy.

However, due to the large amount of fibrous tissue normally present in a human breast, and due to the presence of ligaments running through the breast, a marker that simply has a bright signal alone will not provide a useful signal that can is readily discernable from the many anatomic features normally present within a human breast. Such markers are typically small, being sized to fit within a syringe or other delivery tube, and so are often not readily distinguishable from natural features of the breast, which include occasional small ultrasound-bright spots. Thus, it is generally desirable for an ultrasound-detectable biopsy marker material to provide an ultrasound signal which can be readily differentiated from anatomic structures within the breast, so that the identification and marking of a biopsy cavity does not require extensive training and experience.

A permanent metal or hard plastic, such as a permanent, biocompatible plastic, or other suitable permanent marker may be left at a biopsy site at the completion of a biopsy if the site is to be located again in the future. Suture and collagen-based markers are not considered ideal materials for use as markers because they are hyperechoic, i.e., difficult to see under ultrasound because such materials are easily confused with other shadowing normal structures in the body such as fibrous tissue, fatty tissue, ducts in breast tissue, and the like, for example. Such tissue provides a background clutter that masks the presence of a marker made of metal, hard plastic, or other hyperechoic material.

Water, unlike metal, hard plastic, and other hyperechoic materials, is hypoechoic, i.e., easy to see under imaging techniques such as ultrasound. Therefore, it can be advantageous if a marker made of a hyperechoic material such as metal or hard plastic could be surrounded by an easily seen quantity of water. A hydrogel that has absorbed fluid from surrounding tissue provides such desirable ultrasound characteristics. The marker would become hydrated by natural body moisture after being positioned at a biopsy site, thereby surrounding the permanent marker with water. The water would be easily seen under ultrasound and therefore the permanent marker it surrounds would be easy to see.

The hydration of marker material (122) of carrier (120) by the natural moisture of the tissue surrounding it causes expansion of the polymer and thus minimizes the risk of migration. The growing hydrogel based marker material (122) centers marker (100) in the biopsy cavity as it grows. As the hydrogel expands, naturally-present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of permanent marker (12) within the hydrogel hydrated marker material (122) because the permanent marker (12) is outlined as a specular reflector within a hypoechoic hydrated marker having a water-like nonreflective substrate.

Marker material (122) can be further enhanced by forming air (or aerating fluid) cavities or bubbles within the hydrogel that reflect under ultrasound imaging in a way that differs from the reflection of the hydrogel, making it easier to detect the hydrogel marker material (122). Such air (or aerating fluid) cavities in the enhanced hydrogel are hypoechoic and thus serve to further indicate the location of marker (100). Previously incorporated by reference, U.S. Pat. No. 8,939,910, gives an example of creating air cavities using inserts of differing sizes and shapes. The inserts are placed in the hydrogel during the manufacturing process and removed from the hydrogel after it is cured to leave air-filled cavities in the hydrogel marker. The air-filled cavities image differently under ultrasound than the reflection of the hydrogel and allow the marker to be more easily detected. However, biopsy markers are typically very small, and it can be challenging to use inserts in manufacturing biopsy markers. For example, it can be difficult to remove the inserts from the cured hydrogel.

Aspects presented herein provide a method and system for enhancing a marker material, such as a hydrogel, to form air (or aerating fluid) bubbles in the hydrogel material using at least one aerator, turbulator, mixing device, and/or etc. As will be described in greater detail below, the aerator is generally configured to provide uniform mixing between marker material and air (or aerating fluid) to induce a relatively large quantity of generally fine-sized microbubbles within the marker material. As will also be described in greater detail below, in some instances the combination of the marker material and air (or aerating fluid) is subjected to multiple passes through the aerator to achieve a desired quantity and/or size of microbubbles. Once a desired quantity and/or size of microbubbles has been achieved, the marker material may be cured, dehydrated, etc. as a part of the preparation of the marker.

Aspects presented herein provide methods and apparatuses for providing microbubbles in a marker material with an enhanced quantity, size, and consistency throughout the marker material. These characteristics generally enhance the visibility of the marker material when viewed using ultrasonic imaging. Although certain specific examples and uses are described below, it should be understood that numerous alternative examples and uses may be apparent to those of ordinary skill in the art without departing from the teachings herein.

Figure 2:
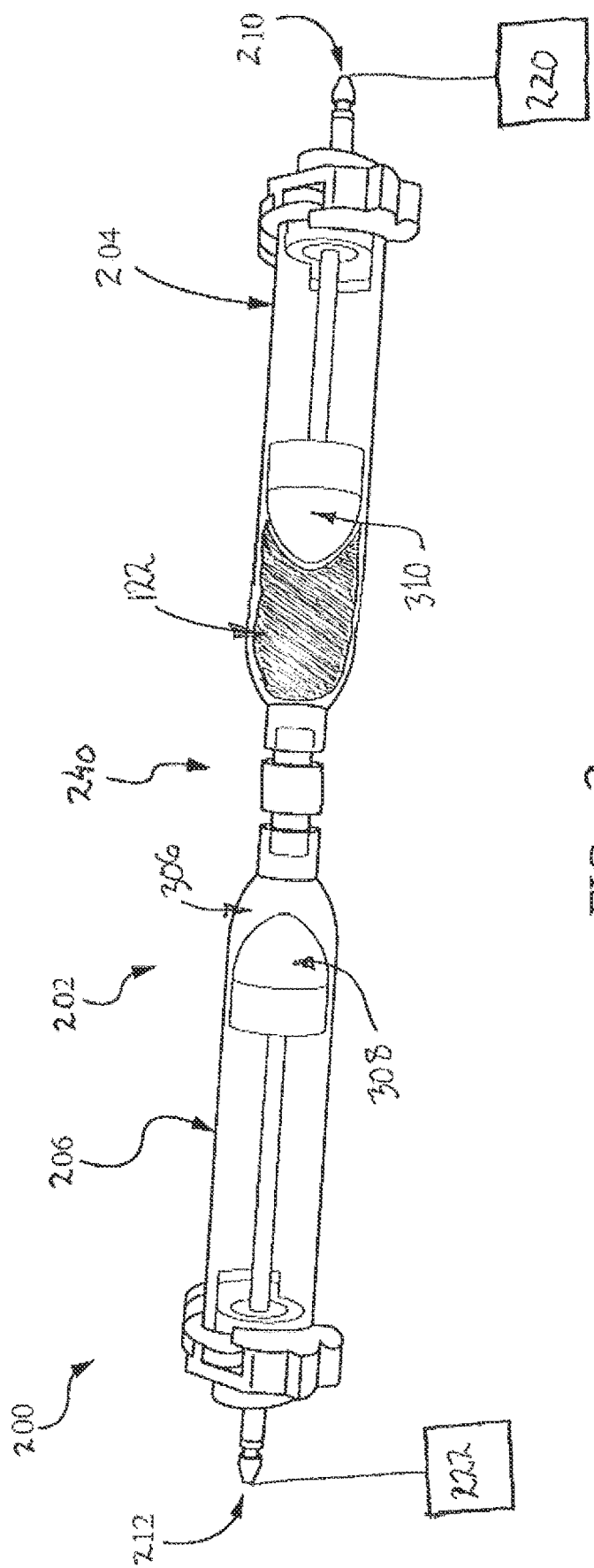
FIG. 2 depicts a perspective view of an exemplary marker material aeration system for use in manufacturing the marker of FIG. 1A.
Figure 3:
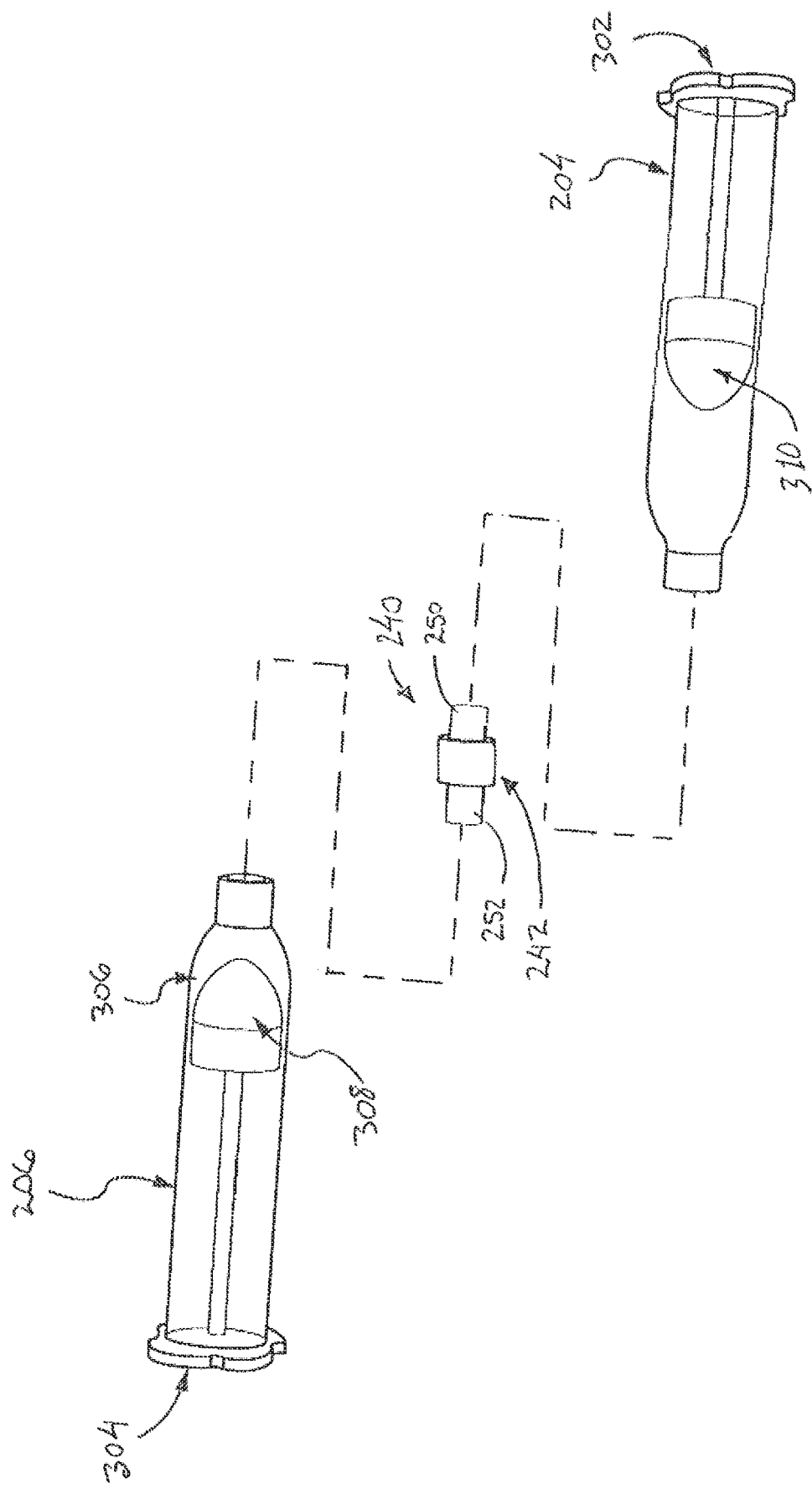
FIG. 3 depicts an exploded perspective view of the marker material aeration system of FIG. 2.

FIGS. 2 and 3 shows an exemplary aeration system (200) for enhancing marker material (122) of biopsy marker (100), described above. System (200) includes a transfer apparatus (202) including two discrete containers (204, 206), two electronic fluid despisers (EFD) (220, 222), and an aeration connection (240) disposed between each container (204, 206). As will be described in greater detail below, transfer apparatus (202) is generally configured to transfer a fluid medium (e.g., air and uncured marker material (122)) between each discrete container (204, 206) to provide aeration to the fluid medium via aeration connection (240).

As described above, transfer apparatus (202) includes two discrete containers (204, 206). Each container (204, 206) is detachably coupled to opposing ends of aeration connection (240). In the present example, each end of aeration connection (240) is configured to act similarly to a standard luer connector such that containers (204, 206) are axially rotatable relative to each other to permit selective coupling and decoupling. In other examples, any suitable type of coupling may be incorporated into aeration connection (240). For instance, in some examples each container (204, 206) may include a barbed or cylindrical tip such that each connector may be coupled to the other by a flexible tube with an interference fit with each barbed tip. In still other examples, each container (204, 206) may include any other suitable connector as will be apparent to those of ordinary skill in the art in view of the teachings herein.

As can be seen in FIG. 3, each container (204, 206) is generally separable from the other container (206, 204) by detaching each container (204, 206) from aeration connection (240). In the present example, each container (204, 206) generally comprises a syringe. The syringes may be selected to both be a dark color or alternatively to both be clear and colorless or one syringe could be a dark color and the other could be clear and colorless. Whether a given syringe is clear, colorless, dark colored, or otherwise, such a syringe may be coated and/or impregnated with materials to block certain specific wavelengths of light. As will be understood, each syringe is generally used in connection with marker material (122). As described above, in some versions marker material (122) is cured using light. Thus, it may be beneficial for each syringe to have light blocking properties to prevent unintended curing of marker material (122). In syringes that are darker or opaque in character, light blocking properties may be inherent. However, in other syringes, additional materials may be required to provide light blocking properties. In still other examples, each syringe may not itself have light blocking properties. Instead, an opaque sheath or other similar structure may be fitted over each syringe to prevent light from entering syringe. By way of example only, in some examples such a sheath can be formed by modifying a standard latex or non-latex exam glove. Of course, other suitable sheaths may be apparent to those of ordinary skill in the art in view of the teachings herein.

Transfer apparatus (202) is generally configured to receive to marker material (122) described above and a selected amount of air (or aerating fluid). For example, unaerated and uncured marker material (122) may be placed in one container (204, 206), and a selected amount of air (or aerating fluid) may be placed in another container (206, 204). Each container (204, 206) may then be alternatingly actuated as described below to transfer the combination of air (or aerating fluid) and uncured marker material (122) through aeration connection (240) between each container (204, 206) to aerate marker material (122).

As seen in FIG. 2, an EFD (220, 222) is coupled to an EFD connection (210, 212) fastened to an open end (302, 304) of each container (204, 206). Each EFD (220, 222) is generally configured to provide a precise pulse of pressurized fluid to each container (204, 206) to transfer marker material (122) between containers (204, 206). Although not shown, it should be understood that in some examples each EFD (220, 222) is coupled to a controller to provide communication between each EFD (220, 222) and/or control of each EFD (220, 222). In some examples, such a controller includes a plurality of switches that provide various circuits to be formed between each EFD (220, 222). By way of example only, such circuits can permit one EFD (220, 222) to communicate a cycle complete signal to another EFD (222, 220) at the conclusion of actuating marker material (122) and air (or aerating fluid) between containers (204, 206). This cycle complete signal may then be used by the other EFD (222, 220) to begin another cycle, actuating marker material (122) and air (or aerating fluid) between containers (204, 206). In some examples, a suitable controller for each EFD (220, 222) can be configured and usable in accordance with at least some of the teachings in U.S. patent Ser. No. 15/636,126, entitled "Method for Enhancing Ultrasound visibility of a Marker," filed on Jun. 28, 2017, the disclosure of which is incorporated by reference herein Although transfer apparatus (202) of the present example is shown as being used with an EFD (220, 222) for each container (204, 206), it should be understood that in other examples only a single EFD may be used with one container (204, 206), while another container (206, 204) may be manually actuated by an operator. In other examples, both EFDs (220, 222) may be omitted entirely. Instead, one or both EFDs may be replaced with an alternative actuation mechanism such as a solenoid, linear actuator, rotary piston driver, or any other suitable mechanism. In some examples, each EFD may be configured and usable in accordance with at least some of the teachings in U.S. patent Ser. No. 15/636,126, entitled "Method for Enhancing Ultrasound visibility of a Marker," filed on Jun. 28, 2017, the disclosure of which is incorporated by reference herein.

As described above, each container (204, 206) includes a corresponding open end (302, 304). Each EFD connection (210, 212) is configured to releasably secured to each open end (302, 304) of each corresponding container (204, 206). This configuration generally permits each container (204, 206) to be opened for insertion of marker material (122) and/or atmospheric air. In the present example, each EFD connection (210, 212) is configured to secure to a corresponding flange protruding outwardly from each container (204, 206) adjacent to each open end (302, 304). However, it should be understood that in other examples each EFD connection (210, 212) may be configured to couple to each container (204, 206) in numerous other ways as will be apparent to those of ordinary skill in the art in view of the teachings herein.

FIG. 2 illustrates an amount of air (or aerating fluid) (306) within container (206) and an amount of marker material (122) within container (204). A plunger (308) maintains the air (or aerating fluid) (306) within container (206), while another plunger (310) maintains marker material (122) within container (204). For example, about 10 cc of marker material (122) (e.g., hydrogel) is maintained within container (204). Within container (206), the selected amount of air (or aerating fluid) (306) may comprise an amount between about 1 cc and about 3 cc, e.g., approximately 2 cc of air (or aerating fluid). In examples using alternative quantities of marker material (122), a ratio of 5:1 marker material (122) to air (or aerating fluid) may generally be maintained.

Figure 4:
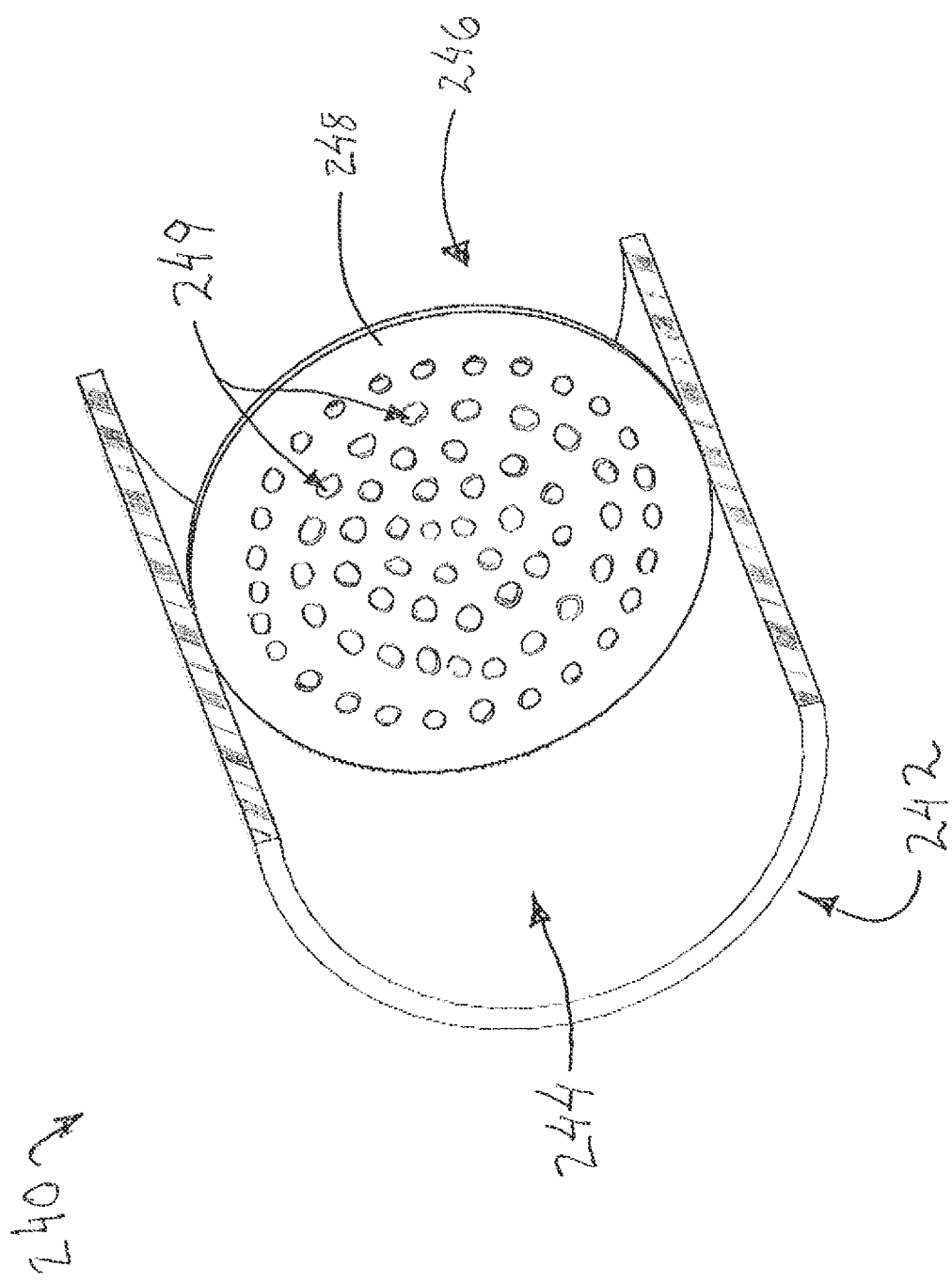
FIG. 4 depicts a perspective cutaway view of an exemplary aeration connection of the aeration system of FIG. 2.

FIGS. 3 and 4 show aeration connection (240) in greater detail. As best seen in FIG. 3, aeration connection (240) comprises an outer body (242) and a pair of opposing connectors (250, 252) protruding from outer body (242). Each connector (250, 252) is generally configured to secure to a corresponding connector on the end of each container (204, 206) to releasably couple each container to aeration connection (240). Although not shown, it should be understood that in some examples each connector (250, 252) is configured as a standard male luer connector such that aeration connection (240) is generally similar to a male-male luer connector. In still other example, each connector (250, 252) may include threading, necking, ribs, or other geometric features configured to facilitate fastening between each connector (250, 252) and each container (204, 206). In other examples, suitable geometric features for coupling may be omitted from each connector (250, 252) and each connector (250, 252) may instead couple to each respective container (204, 206) using an interference fitting or any other fitting as will be apparent to those of ordinary skill in the art in view of the teachings herein.

Outer body (242) is generally hollow with a generally cylindrical shape. As best seen in FIG. 4, the interior of outer body (242) defines a lumen (244) extending therethrough. Although not shown, it should be understood that lumen (244) is defined by aeration connection (240) to generally extend axially entirely through aeration connection (240). As will be described in greater detail below, this configuration permits fluid to be transferred from one container (204, 206) to the other container (206, 204) for the purposes of aeration.

The interior of outer body (242) further includes a screen disk (246) disposed transversely within lumen (244). Screen disk (246) includes a disk-shaped screen body (248) with a plurality of bores (249) extending through body (248). Screen body (248) generally defines a plane that is oriented perpendicularly relative to a longitudinal axis defined by outer body (242). Although screen body (248) of the present example is generally oriented perpendicularly, it should be understood that in other examples screen body (248) can be oriented at a variety of other angles relative to the longitudinal axis defined by outer body (242). Screen body (248) is generally sized to correspond to the inner diameter of outer body (242). As will be described in greater detail below, this configuration substantially seals lumen (244) to force fluid through bores (249) instead of freely through lumen (244).

As described above, screen disk (246) includes a plurality of bores (249). As will be described in greater detail below, bores (249) are generally sized and arranged to promote aeration of fluid as the fluid flows through screen disk (246). In the present example, bores (249) are arranged in a generally circular pattern across the face of screen body (248). Although bores (249) are shown as being arranged in a particular pattern in the present example, it should be understood that in other examples bores (249) may be arranged in numerous alternative configurations.

Each bore (249) is generally sized with an area that is smaller than the area of lumen (244) to introduce some turbulence in any fluid flowing through a particular bore (249). In the present example, where a combination of air (or aerating fluid) and uncured marker material (122) is used, this turbulence generally breaks up the flow of combination of air (or aerating fluid) and maker material (122) into smaller drops, thereby promoting uniform distribution of relatively small microbubbles.

The size of each bore (249) is therefore generally related to the size of the microbubbles formed in uncured marker material (122). It should be understood that a desirable size of the microbubbles is related to the wavelength of the ultrasonic beam used for identifying biopsy marker (100). In some examples the diameter of a given microbubble is substantially less than the wavelength of the beam. For example, an ultrasonic beam at 3.5 MHz has a wavelength of about 17,000 microns, whereas an ultrasonic beam at 7.5 MHz has a wavelength of about 8,000 microns. As the frequency of more advanced high definition ultrasound scanners approaches 35 MHz and greater, it would be preferable to have the size of each bore (249) in diameter be 1000 microns or less. In other examples, the size of each bore (249) is 500 microns or less in diameter for a substantial improvement in the ultrasonic images for any types of ultrasonic equipment. In other examples, each bore (249) is sized approximately 150 microns in diameter. Although each bore (249) is shown in the present example as being generally similar in size relative to each other bore (249), it should be understood that in other examples each bore (249) may vary in size in accordance with a random pattern or a predetermined pattern. In addition, although the above-referenced sizes imply a generally circular shape by being in terms of diameter, it should be understood that each bore (249) may take on a variety of shapes (e.g., square, rectangle, oval-shaped, irregular and/or etc.). As such, where an alternative shape is used, each of the above-referenced sizes may correspond to the highest width of a given bore (249).

Although screen disk (246) is shown and described herein as being generally configured as a disk with several bores (249) or holes, it should be understood that in other examples screen disk (246) can take on a variety of other configurations. For instance, in some examples screen disk (246) comprises a mesh screen secured to the interior of outer body (242). In yet other examples, screen disk (246) is a porous elongate structure comprising a pliable membrane or rigid porous structure. In addition, although the present example is shown as including a single screen disk (246), it should be understood that in other examples multiple screen disks (246) of the same or different configuration may be used. In examples where screen disk (246) described herein is essentially duplicated to include two screen disks (246), each screen disk (246) can be positioned to misalign bores (249) or other similar structures relative to corresponding bores (249) of the other screen disk (246). In addition, to facilitate flow through each screen disk (246), each screen disk (246) can be circumferentially offset from the other screen disk (246). In one example, each screen disk (246) (or a flexible screen/mesh material) may be secured into opposite sides of a luer coupler.

Figure 5:
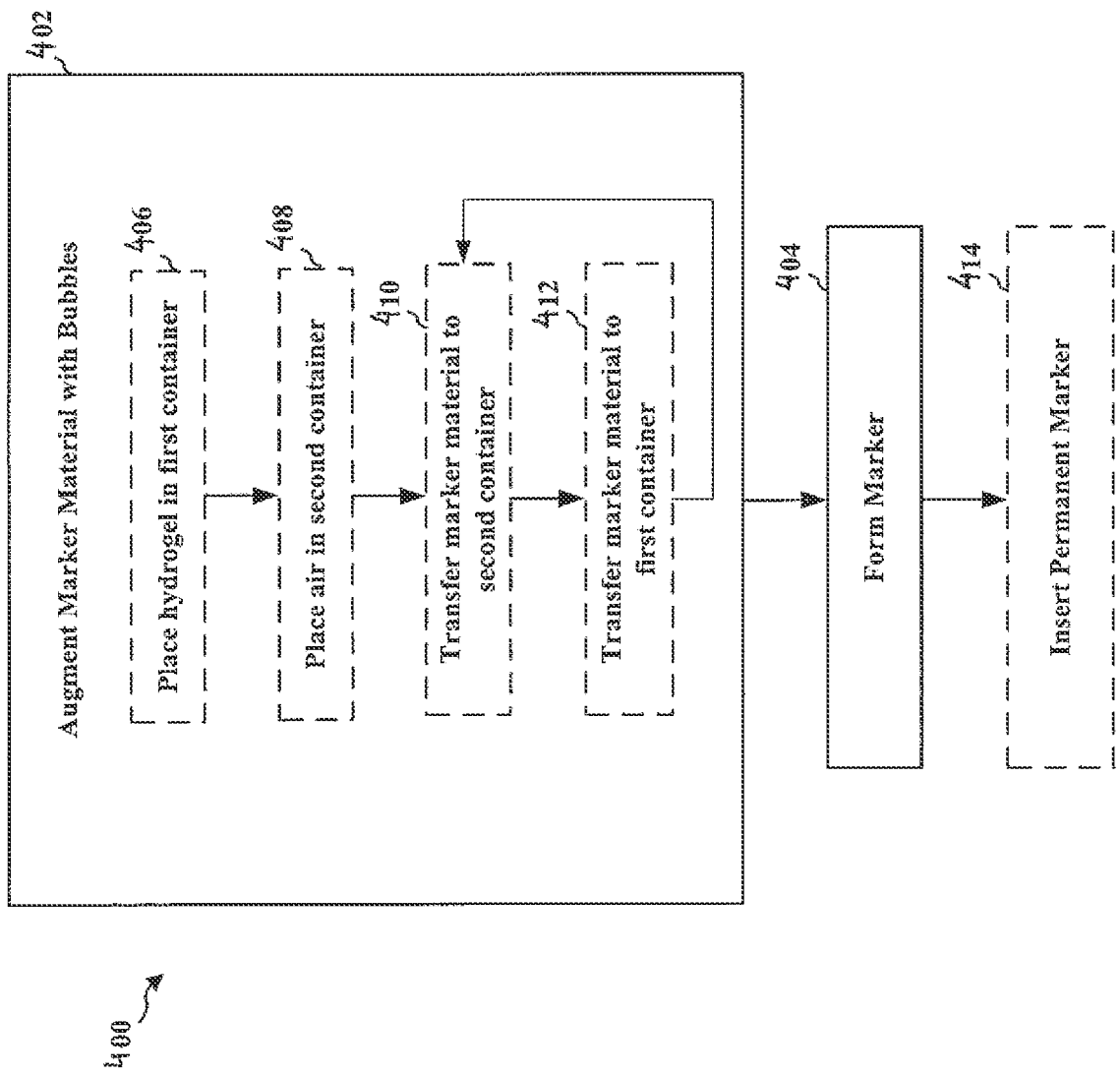
FIG. 5 depicts a flowchart of an exemplary method for using the aeration system of FIG. 2 for manufacturing the marker of FIG. 1A.

FIG. 5 shows a flow chart of an exemplary method (400) of manufacturing a marker, such as marker (100) described above. The method may be performed, for example, using an aeration system such as systems (200) described above. The steps in FIG. 2 that are shown in phantom may optionally be repeated multiple times. At item (402), a marker material similar to marker material (122) described above is enhanced to include a plurality of air bubbles, aerating fluid bubbles, or air cavities, using at least EFDs (220, 222) described above. Then, at item (404), a marker is formed using the enhanced marker material (122). As described above, marker material (122) may comprise a bioabsorbable material such as a hydrogel.

Enhancing marker material (122) at item (402) includes cycling repeatedly through a transfer process between containers (204, 206). For example, the transfer process may include transferring marker material (122) from container (204) to container (206) using the EFD (220) at item (410). Then, marker material (122) may then be returned to the container (204) by transferring the marker material (122) from container (206) back to container (204) using EFD (222) at item (412). As illustrated in FIG. 5, marker material (122) may be repeatedly transferred back and forth between the two containers (204, 206) by alternately driving the two EFDs (220, 222). Alternatively, in some uses EFDs (220, 222) may be omitted and marker material (122) may be repeatedly transferred back and forth between two containers (204, 206) via manual actuation. As marker material (122) is transferred between containers (204, 206), marker material (122) in combination with air (or aerating fluid) passes through bores (249) of screen disk (246) disposed within aeration connection (240). This process breaks up large air (or aerating fluid) bubbles disposed within marker material (122) into progressively smaller and more dispersed air (or aerating fluid) bubbles. This cycle may automatically continue for a predetermined number of transfers and stop. Alternately, the cycle may continue until an operator stops the cycle.

Figure 6A:
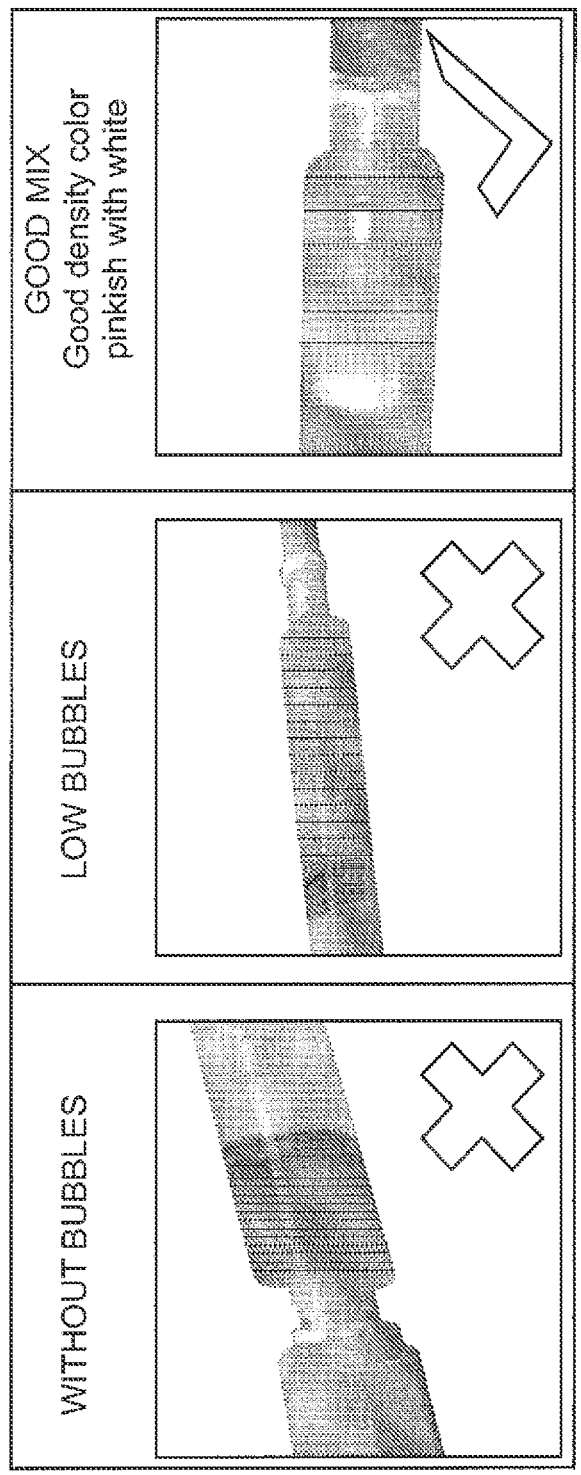
FIG. 6A depicts a series view of an exemplary visual inspection that may be performed during the method of FIG. 4.
Figure 6B:
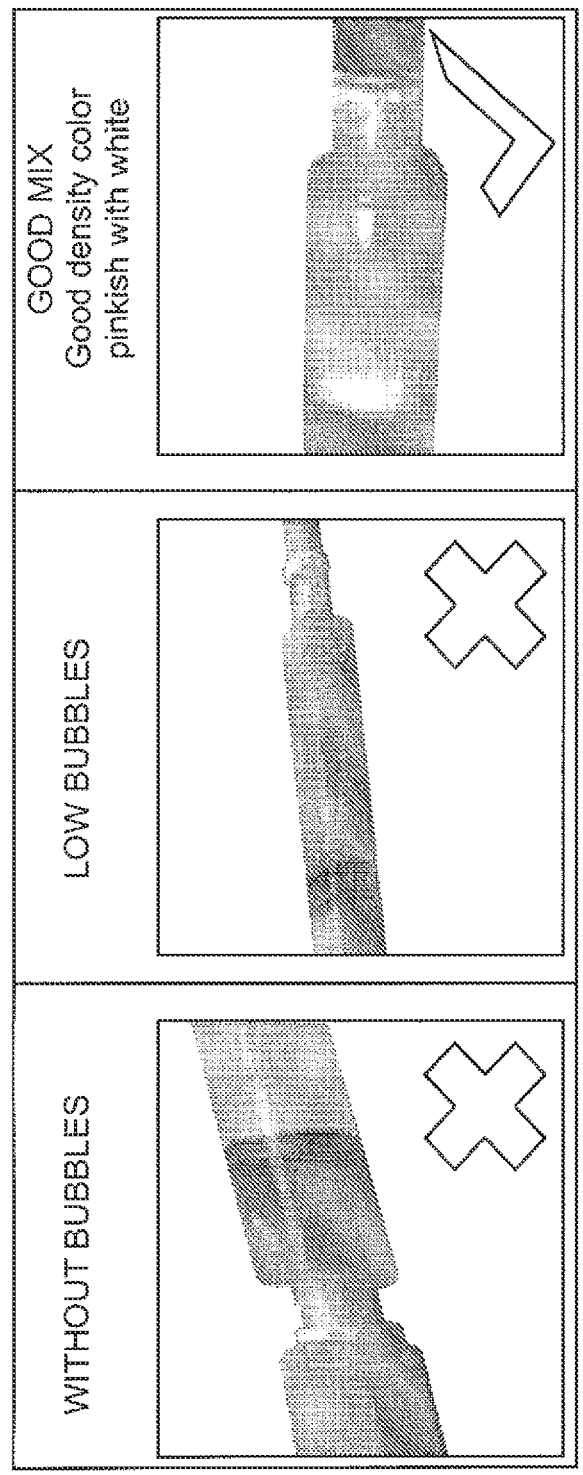
FIG. 6B depicts another series view of the visual inspection of FIG. 5A.

After performing the steps illustrated within item (402) for a desired number of cycles, an inspection of the aerated marker material (122) may be made. An acceptable mixture of air (or aerating fluid) into a hydrogel marker material may have a discernible (pinkish) color contrasting with (white) air (or aerating fluid) bubbles, as illustrated in FIGS. 6A and 6B. The bubbles may be visible in the enhanced marker material. FIG. 6A illustrates a black and white drawing showing the change in the hydrogel to include bubbles, and FIG. 6B is a photo illustration of the visible change in the hydrogel. If an additional amount of air (or aerating fluid) bubbles is desired, the cycle of the steps illustrated by item (410) to item (412) may be repeated. The repeat may include a reduced number of cycles from the original transfer process or may include the same number of cycles as the original transfer process.

As illustrated at item (404), the method may further include forming marker (100). Carrier (120) is initially formed by molding or manipulating marker material (122) into a desirable shape for marker (100). In some examples, this step can include injecting or otherwise inserting marker material (122) into a plurality of pill-shaped containers generally corresponding to the final shape and size of carrier (120). In such examples, each pill-shaped container may be clear or transparent to permit at least some curing of marker material (122) through the container.

After carrier (120) is formed, item (414) illustrates inserting one or more permanent markers (12) into the formed carrier (120). During this step, permanent marker (12) can be inserted into marker material (122) of carrier (120) using a manipulator such as a rigid wire, tube, and/or etc. The manipulator may then be extracted from marker material (122) after placement of permanent marker (12) within marker material (122). It should be understood that during this stage, marker material (122) may be uncured or partially cured. Partial curing can be used to assist with positioning and temporarily fixing permanent marker (12). For instance, in the circumstance of partially cured marker material (122), a manipulator may be used to insert permanent marker (12) into marker material (122). Once permanent marker (12) is positioned within marker material (122), the partially cured marker material (122) can be viscous enough to hold permanent marker (12) in position without support of the manipulator. Thus, when permanent marker (12) is inserted wile marker material (122) is partially cured, manipulator may be removed without permanent marker (12) moving out of position.

After carrier (120) is formed at item (404) and one or more permanent markers (12) are inserted at item (414), the marker (100) may be cured and/or dehydrated, as additional aspects of the manufacturing process. In examples where marker material (122) is hydrogel, the curing process may be performed by applying light of various wavelengths to the marker (100). Light may be applied until marker material (122) is fully cured. In some examples, light may be applied for a limited period to partially cure marker material (122). In the partially cured state, marker material (122) may be cured to substantially fix permanent marker (12) within marker material (122). At the same time, the curing of marker material (122) may be substantially limited to permit extraction of manipulators or other support structures related to placing permanent marker (12) within marker material (122). Once such structures are removed, light may be applied again to fully cure marker material (122).

Although not shown, it should be understood that in some examples system (200) of the present example further includes a controller or other unit that is in communication with each EFD (220, 222) to controls the transfer process between each container (204, 206) via each EFD (220, 222). Such a controller can include various user interface features such as a power switch, a restart button, and/or a cycle selector switch. Such user interface features may be suitable for operating system (200) via each EFD (220, 222). In some examples, such a controller may be configured and operable in accordance with at least some of the teachings in U.S. patent Ser. No. 15/636,126, entitled "Method for Enhancing Ultrasound Visibility of a Marker," filed on Jun. 28, 2017, the disclosure of which is incorporated by reference herein.

Figure 7:
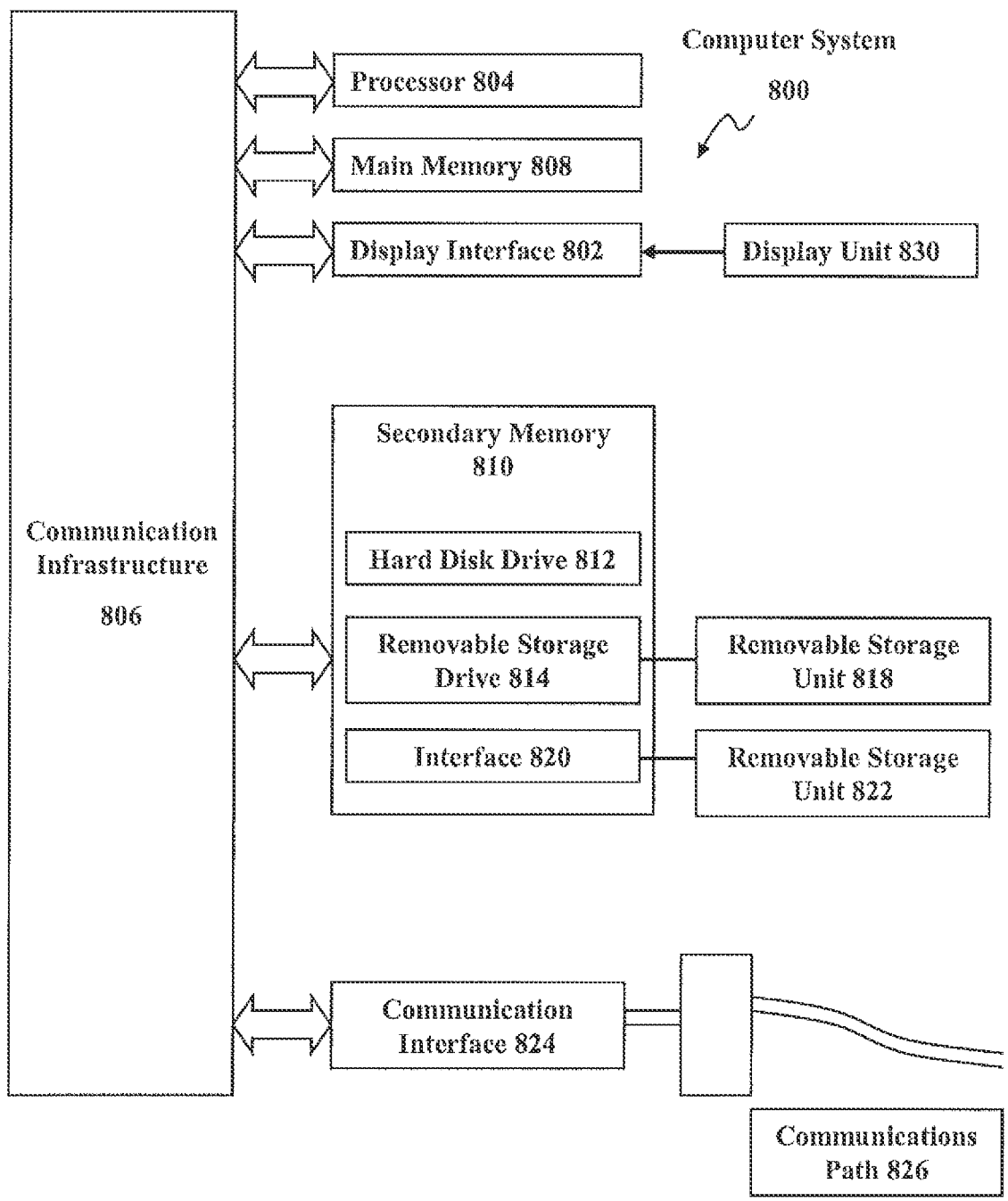
FIG. 7 depicts an exemplary system diagram of various hardware components and other features that may be readily incorporated into the aeration system of FIG. 2.

FIG. 7 presents an exemplary system diagram of various hardware components and other features, for use in accordance with aspects presented herein. The aspects may be implemented using hardware, software, or a combination thereof and may be implemented in one or more computer systems or other processing systems. In one example, the aspects may include one or more computer systems capable of carrying out the functionality described herein, for example aspects described in connection with FIG. 5, e.g., items 402, 410, 412, etc. An example of such a computer system (800) is shown in FIG. 7.

Computer system (800) includes one or more processors, such as processor (804). The processor (804) is connected to a communication infrastructure (806) (e.g., a communications bus, cross-over bar, or network). Various software aspects are described in terms of this example computer system. After reading this description, it will become apparent to a person skilled in the relevant art(s) how to implement the aspects presented herein using other computer systems and/or architectures.

Computer system (800) can include a display interface (802) that forwards graphics, text, and other data from the communication infrastructure (806) (or from a frame buffer not shown) for display on a display unit (830). Computer system (800) also includes a main memory (808), preferably random access memory (RAM), and may also include a secondary memory (810). Secondary memory (810) may include, for example, a hard disk drive (812) and/or a removable storage drive (814), representing a floppy disk drive, a magnetic tape drive, an optical disk drive, etc. Removable storage drive (814) reads from and/or writes to a removable storage unit (818) in a well-known manner. Removable storage unit (818), represents a floppy disk, magnetic tape, optical disk, etc., which is read by and written to removable storage drive (814). As will be appreciated, the removable storage unit (818) includes a computer usable storage medium having stored therein computer software and/or data.

In alternative aspects, secondary memory (810) may include other similar devices for allowing computer programs or other instructions to be loaded into computer system (800). Such devices may include, for example, a removable storage unit (822) and an interface (820). Examples of such may include a program cartridge and cartridge interface (such as that found in video game devices), a removable memory chip (such as an erasable programmable read only memory (EPROM), or programmable read only memory (PROM)) and associated socket, and other removable storage units (822) and interfaces (820), which allow software and data to be transferred from the removable storage unit (822) to computer system (800).

Computer system (800) may also include a communications interface (824). Communications interface (824) allows software and data to be transferred between computer system (800) and external devices. For instance, in some examples communication interface (824) is in communication with one or more EFDs (220, 222). In still other examples, computer system (800) may be fully or partially integrated into one or more EFDs (220, 222) such that communication interface (824) is disposed entirely within the one or more EFDs (220, 222).

Examples of communications interface (824) may include a modem, a network interface (such as an Ethernet card), a communications port, a Personal Computer Memory Card International Association (PCMCIA) slot and card, etc. Software and data transferred via communications interface (824) are in the form of signals, which may be electronic, electromagnetic, optical or other signals capable of being received by communications interface (824). These signals are provided to communications interface (824) via a communications path (e.g., channel) (826). This path (826) carries signals and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive (880), a hard disk installed in hard disk drive (870), and signals. These computer program products provide software to the computer system (800). Aspects presented herein may include such computer program products.

Computer programs (also referred to as computer control logic) are stored in main memory (808) and/or secondary memory (810). Computer programs may also be received via communications interface (824). Such computer programs, when executed, enable the computer system (800) to perform the features presented herein, as discussed herein. In particular, the computer programs, when executed, enable the processor (810) to perform the features presented herein. Accordingly, such computer programs represent controllers of the computer system (800).

In aspects implemented using software, the software may be stored in a computer program product and loaded into computer system (800) using removable storage drive (814), hard drive (812), or communications interface (820). The control logic (software), when executed by the processor (804), causes the processor (804) to perform the functions as described herein. In another example, aspects may be implemented primarily in hardware using, for example, hardware components, such as application specific integrated circuits (ASICs). Implementation of the hardware state machine so as to perform the functions described herein will be apparent to persons skilled in the relevant art(s).

In yet another example, aspects presented herein may be implemented using a combination of both hardware and software.

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system for aerating a marker material, the system comprising: a first container, a second container, and an aeration connector including a body and a screen disk disposed within the body, wherein the first container is in communication with the second container via the aeration connector, wherein the screen disk of the aeration connector is configured to aerate a marker material as the marker material is repeatedly passed between the first container and the second container.

Example 2

The system of Example 1, wherein the first container comprises a syringe, wherein the second container includes a syringe.

Example 3

The system of any one or more of Examples 1 through 2, the aeration connector includes a first luer connector and a second luer connector, wherein the first container is configured to couple to the first luer connector, wherein the second container is configured to couple to the second luer connector.

Example 4

The system of any one or more of Examples 1 through 3, wherein the screen disk of the aeration connector includes a plurality of bores extending through a portion of the screen disk.

Example 5

The system of Example 4, wherein each bore of the plurality of bores is sized with a diameter of 25 to 500 microns.

Example 6

The system of Example 4, wherein each bore of the plurality of bores is sized with a diameter of approximately 150 microns.

Example 7

The system of any one or more of Examples 1 through 3, wherein the screen disk is defined by a screen.

Example 8

The system of any one or more of Examples 1 through 7, wherein the aeration connector includes two screen disks.

Example 9

The system of any one or more of Examples 1 through 8, further comprising at least one electronic fluid dispenser (EFD), wherein the at least one EFD is configured to drive the marker material between the first container and the second container.

Example 10

The system of any one or more of Examples 1 through 7, wherein the body of the aeration connector defines a longitudinal axis, wherein the body is configured to direct the marker material through the aeration connector along the longitudinal axis.

Example 11

The system of Example 10, wherein the screen disk defines a plane oriented perpendicularly relative to the longitudinal axis defined by the aeration connector.

Example 12

The system of any one or more of Examples 1 through 7 and 10 through 11, wherein the body of the aeration connector defines a cylindrical hollow interior.

Example 13

The system of Example 12, wherein the screen disk includes an outer diameter that is equivalent to an inner diameter of the hollow interior of the body of the aeration connector.

Example 14

The system of Example 12, wherein the screen disk is sized relative to the hollow interior of the body of the aeration connector such that screen disk is configured to force marker material through at least a portion of the screen disk as the marker material flows through the aeration connector.

Example 15

A system for enhancing a marker material, the system comprising: a first container configured to receive a marker material, a second container configured to receive a selected amount of air; a coupler disposed between the first container and the second container, wherein the coupling includes an aerator, wherein at least a portion of the aerator defines a plurality of openings that are configured to disperse progressively smaller microbubbles of the selective amount of air into the marker material as the marker material is transferred from between the first container and the second container.

Example 16

The system of Example 15, wherein a first end of the first container comprises a first opening to which a first EFD is coupled and a second end of the second container comprises a second opening opposite the first opening, a second EFD being coupled to the second opening.

Example 17

The system of any one or more of Examples 15 through 16, wherein the first container and the second container includes a first syringe coupled to a second syringe via the coupler.

Example 18

The system of any one or more of Examples 15 through 17, wherein the openings of the aerator are arranged in a circular pattern.

Example 19

The system of any one or more of Examples 15 through 17, wherein the openings of the aerator are arranged in a random pattern.

Example 20

A system for aerating a marker material, the system comprising: a first portion, a second portion, and an aerator disposed between the first portion and the second portion, wherein the aerator includes a body defining a plurality of openings, wherein the first portion is in communication with the second portion via the aerator, wherein the body of the aerator is configured to aerate a marker material as the marker material is repeatedly passed between the first portion and the second portion.

Example 21

A method of manufacturing a marker comprising: connecting to each other first and second containers associated with respective first and second electronic fluid dispensers (EFDs); initiating an aeration cycle with the first and second EFDs such that marker material is moved back and forth between the first and second containers to create an aerated marker material; and directing the marker material through a body including a plurality of aeration openings as the marker material is moved back and forth between the first and second containers to further aerate the aerated marker material.

Example 22

A system for manufacturing aerated hydrogel comprising: a first container for containing hydrogel material; a second container for containing aerating fluid; a coupler positioned between and having a lumen in fluid communication with the first and second containers; and a filter positioned in a fluid communication path between the first and second containers and having a plurality of openings with each opening having a smaller area than the lumen of the coupler.

Example 23

The system of Example 22, further comprising first and second transfer rods that transfer the hydrogel material and the aerating fluid between the first and second containers through the filter and the coupler to mix the hydrogel material and the aerating fluid together to create the aerated hydrogel.

Example 24

The system of any one or more of Examples 22 and 23, wherein the highest width of at least one opening of the filter is 1000 microns or less.

Example 25

The system of any one or more of Examples 22 and 23, wherein the filter includes a disk having a plurality of round openings with each opening having a diameter of 1000 microns or less.

Example 26

The system of any one or more of Examples 22 through 25, wherein the filter includes first and second filters spaced from each other.

Example 27

The system of any one or more of Examples 22 through 25, wherein the filter includes first and second filters spaced and circumferentially offset from each other.

Example 28

The system of any one or more of Examples 22 through 27, wherein the coupler includes a luer coupler and the filter is positioned inside the luer coupler.

Example 29

The system of any one or more of Examples 22 through 27, wherein the coupler includes a luer coupler and the filter includes first and second filters spaced from each other and positioned inside the luer coupler.

Example 30

The system of any one or more of Examples 22 through 29, wherein the first and second containers include first and second syringes, the system further comprising an automatic fluid dispenser configured to automatically transfer the fluid and hydrogel material back and forth between the first and second containers through the coupler and the filter.

Example 31

The system of any one or more of Examples 22 through 24, wherein the filter includes a mesh filter whose openings are 500 microns or less.

Example 32

A system for manufacturing an aerated hydrogel comprising: a first syringe for containing hydrogel material and having a first plunger; a second syringe for containing aerating fluid and having a second plunger; a coupler positioned between and having a lumen in fluid communication with the first and second syringes; and a filter positioned in the coupler and in fluid communication with the first and second syringes, the filter having a plurality of openings with each opening having a smaller area than the lumen of the coupler so as to disperse the aerating fluid and the hydrogel; the first and second plungers transferring the hydrogel material and the aerating fluid between the first and second syringes through the filter to mix the hydrogel material and the aerating fluid together to create the aerated hydrogel.

Example 33

The system of Example 32, wherein the highest width of at least one opening of the filter is 1000 microns or less.

Example 34

The system of Example 32, wherein the filter includes a disk having a plurality of round openings with each opening having a diameter of 1000 microns or less.

Example 35

The system of any one or more of Examples 32 through 34, wherein the coupler includes a luer coupler and the filter includes first and second filters spaced from each other and positioned inside the luer coupler.

Example 36

The system of any one or more of Examples 32 through 35, further comprising an automatic fluid dispenser configured to automatically transfer the fluid and hydrogel material back and forth between the first and second syringes through the coupler and the filter.

Example 37

The system of Example 32, wherein the filter includes a mesh filter whose openings are 500 microns or less.

Example 38

A method of manufacturing an aerated hydrogel comprising: inserting hydrogel material in a first container; inserting aerating fluid in a second container; coupling the first and second containers together through a lumen of a coupler; and transferring the inserted hydrogel and the inserted aerating fluid back and forth between the first and second containers through a filter positioned in a fluid communication path between the first and second containers and having a plurality of openings with each opening having a smaller area than the lumen of the coupler.

Example 39

The method of Example 38, wherein the step of transferring includes transferring the inserted hydrogel and the inserted aerating fluid back and forth between the first and second containers through the filter whose highest width of at least one opening is 1000 microns or less.

Example 40

The method of Example 38, wherein the step of transferring includes transferring the inserted hydrogel and the inserted aerating fluid back and forth between the first and second containers through first and second filters spaced from each other.

Example 41

The method of any one or more of Examples 38 through 40, wherein the step of transferring includes automatically transferring the fluid and hydrogel material back and forth between the first and second containers through the coupler and the filter using an automatic fluid dispenser.

Example 42

The method of Example 38, wherein the step of transferring includes transferring the inserted hydrogel and the inserted aerating fluid back and forth between the first and second containers through first and second filters spaced from each other.

Example 43

The method of Example 38, wherein the step of transferring includes transferring the inserted hydrogel and the inserted aerating fluid back and forth between the first and second containers through a mesh filter whose openings are 500 microns or less.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method of manufacturing an aerated hydrogel comprising:
    inserting hydrogel material in a first container;
    inserting aerating fluid in a second container;
    coupling the first and second containers together through a lumen of a coupler; and
    transferring the inserted hydrogel and the inserted aerating fluid back and forth between the first and second containers through a filter positioned in a fluid communication path between the first and second containers and having a plurality of openings with each opening having a smaller area than the lumen of the coupler such that each opening is configured to introduce turbulence in the hydrogel or the aerating fluid.

2. The method of claim 1, wherein the step of transferring includes transferring the inserted hydrogel and the inserted aerating fluid back and forth between the first and second containers through the filter whose highest width of at least one opening is 1000 microns or less.

3. The method of claim 1, wherein the step of transferring includes transferring the inserted hydrogel and the inserted aerating fluid back and forth between the first and second containers through first and second filters spaced from each other.

4. The method of claim 1, wherein the step of transferring includes automatically transferring the fluid and hydrogel material back and forth between the first and second containers through the coupler and the filter using an automatic fluid dispenser.

5. The method of claim 1, wherein the step of transferring includes transferring the inserted hydrogel and the inserted aerating fluid back and forth between the first and second containers through first and second filters spaced from each other.

6. The method of claim 1, wherein the step of transferring includes transferring the inserted hydrogel and the inserted aerating fluid back and forth between the first and second containers through a mesh filter whose openings are 500 microns or less.

* * * * *